US008696568B2

(12) United States Patent
Jedwab et al.

(10) Patent No.: US 8,696,568 B2
(45) Date of Patent: Apr. 15, 2014

(54) METHODS, SYSTEM AND KIT FOR DIAGNOSING AND TREATING DYSPHAGIA

(75) Inventors: Michael Rueben Jedwab, Lausanne (CH); Zamzam Kabiry Roughead, Plymouth, MN (US); Kala Marie Kaspar, Lausanne (CH); Armando Sanchez, Saint-Sulpice (CH); Christoph Hartmann, Epalinges (CH); Chrystel Loret, Lausanne (CN); Nathalie Martin, Lausanne (CH); Jan Engmann, Epalinges (CH)

(73) Assignee: Nestec S.A., Vevey (CH)

( * ) Notice: Subject to any disclaimer, the term of this patent is extended or adjusted under 35 U.S.C. 154(b) by 170 days.

(21) Appl. No.: 13/144,605

(22) PCT Filed: Dec. 7, 2009

(86) PCT No.: PCT/US2009/066972
§ 371 (c)(1),
(2), (4) Date: Sep. 20, 2011

(87) PCT Pub. No.: WO2010/082986
PCT Pub. Date: Jul. 22, 2010

(65) Prior Publication Data
US 2012/0046641 A1 Feb. 23, 2012

Related U.S. Application Data

(60) Provisional application No. 61/120,690, filed on Jan. 15, 2009, provisional application No. 61/240,789, filed on Sep. 9, 2009, provisional application No. 61/258,232, filed on Nov. 5, 2009.

(51) Int. Cl.
*A61M 31/00* (2006.01)
*G09B 19/00* (2006.01)
*A23L 1/05* (2006.01)
*A23L 1/0522* (2006.01)
*A23L 1/0526* (2006.01)
*A23K 1/18* (2006.01)
*G06F 19/00* (2011.01)
*A61B 5/00* (2006.01)

(52) U.S. Cl.
CPC .......... *G06F 19/3431* (2013.01); *G06F 19/34* (2013.01); *G06F 19/3437* (2013.01); *G06F 19/3487* (2013.01); *G06F 19/36* (2013.01); *G06F 19/363* (2013.01); *A23L 1/05* (2013.01); *A23L 1/0522* (2013.01); *A23L 1/0526* (2013.01); *A23K 1/1846* (2013.01); *A61B 2505/03* (2013.01); *A61B 2505/07* (2013.01); *A61B 2505/09* (2013.01); *Y10S 128/92* (2013.01); *Y10S 128/921* (2013.01); *Y10S 128/922* (2013.01); *Y10S 128/923* (2013.01); *Y10S 128/924* (2013.01)
USPC ......... 600/300; 128/920; 128/921; 128/922; 128/923; 128/924; 705/2; 705/3; 428/402; 514/772; 514/774; 426/573; 426/648; 434/127

(58) Field of Classification Search
CPC . G06F 19/3431; G06F 19/34; G06F 19/3437; G06F 19/3487; G06F 19/36; G06F 19/363; A23L 1/05; A23L 1/0522; A23L 1/0526; A23L 1/0528; A23K 1/1846; A61B 2505/03; A61B 2505/07; A61B 2505/09
USPC .................. 705/2–3; 600/300; 128/920–925; 428/402; 514/772, 774; 426/573, 648; 434/127
See application file for complete search history.

(56) References Cited

U.S. PATENT DOCUMENTS

| 5,976,084 | A | 11/1999 | Tymchuck et al. | |
|---|---|---|---|---|
| 6,592,863 | B2 * | 7/2003 | Fuchs et al. | 424/93.1 |
| 7,593,952 | B2 * | 9/2009 | Soll et al. | 1/1 |
| 2003/0044351 | A1 * | 3/2003 | Robbins | 424/9.1 |
| 2004/0197456 | A1 * | 10/2004 | Holahan | 426/573 |
| 2009/0074940 | A1 * | 3/2009 | Sliwinski | 426/648 |
| 2010/0074993 | A1 * | 3/2010 | Cooreman et al. | 426/61 |
| 2010/0311686 | A1 * | 12/2010 | Kasper et al. | 514/54 |

Dysphagia Patient Management Algorithm

FOREIGN PATENT DOCUMENTS

JP 2003111748 4/2003

OTHER PUBLICATIONS

Manor, Y. A. et al; "Validation of a Swallowing Disturbance Questionnaire for Detecting Dysphagia in Patients with Parkinson's Disease"; Movement Disorders, vol. 22, No. 13, 2007, p. 1917-1921.*
Surayanarayanan, S. et al "A fuzzy logic diagnosis system for classification of pharyngeal dysphagia" International Journal of Bio-Medical Computing 38 (1995) 207-215.*
Palmer, J. B. et al "Evaluation and Treatment of Swallowing Impairments"; Am Fam Physician. Apr. 15, 2000;61(8):2453-2462.*
Clave, P et al; "Accuracy of the volume-viscosity swallow test for clinical screening of oropharyngeal dysphagia and aspiration"; Clinical Nutrition (2008) 27, 806-815.*
EAT-10 Swallowing-Difficulty Survey, 2008, p. 1.*
FAQ's on Swallowing Screening, FAQ originally developed in 2006 by members of the Steering Committee of Special Interest Division 13 (Swallowing and Swallowing Disorders) of the American Speech-Language-Hearing Association, p. 1-11, 2006.*
Fleming, M. et al; "Index of Dysphagia: A tool for Identifying Deglutition Problems"; Dysphagia, 1, 1987, p. 206-208.*
Kiger, M. et al "Dysphagia Management: An Analysis of Patient Outcomes Using VitalStimTM Therapy Compared to Traditional Swallow Therapy"; Dysphagia 2006: 243-253.*
Tytgat, G. N. et al; "New algorithm for the treatment of gastro-oesophageal reflux Disease"; (20070); Aliment Pharmacol Ther 27, 249-256.*
Bulow et al., "Videoradiographic Analysis Of How Carbonated Thin Liquids And Thickened Liquids Affect The Physiology Of Swallowing In Subjects With Aspiration On Thin Liquids", ACTA Radiologica, 2003, pp. 366-372, vol. 44, No. 4.
Chee, "The Influence of Chemical Gustatory Stimuli and Oral Anaesthesia on Healthy Human Pharyngeal Swallowing", Chem. Senses, 2005, pp. 393-400, vol. 30.
Ding et al., "The Effects of Taste and Consistency on Swallow Physiology in Younger and Older Healthy Individuals: A Surface Electromyographic Study", Journal of Speech, Language and Hearing Research, Aug. 2003, pp. 977-989, vol. 46.
Garcia et al., "Thickened Liquids: Practice Patterns of Speech-Language Pathologists", Am. Journal of Speech-Language Pathology, Feb. 2005, pp. 4-13, vol. 14.
Hamdy et al., "Modulation of human swallowing behaviour by thermal and chemical stimulation in health and after brain injury", Neurogastroenterol Motil, 2003, pp. 69-77, vol. 15.
Kaatzke-McDonald et al., "The Effects of Cold, Touch, and Chemical Stimulation of the Anterior Faucial Pillar on Human Swallowing", Dysphagia, 1996, pp. 198-206, vol. 11.
Leow et al., The Influence of Taste on Swallowing Apnea, Oral Preparation Time, and Duration and Amplitude of Submental Muscle Contraction, Chem. Senses, 2007, pp. 119-128, vol. 32.
Logemann et al., "Effets of a Sour Bolus on Oropharyngeal Swallowing Measures in Patients With Neurogenic Dysphagia", Journal of Speech and Hearing Research, Jun. 1995, pp. 556-563, vol. 38.
Logemann, "Treatment for Aspiration Related to Dysphagia: An Overview", Dysphagia, 1986, pp. 34-38, vol. 1.
Lotong et al., "Categorization of Commercial Orange Juices Based on Flavor Characteristics", Journal of Food Science, 2003, pp. 722-725, vol. 66, No. 2.
Welge-Lussen et al., "Swallowing is Differentially Influenced by Retronasal Compared with Orthonasal Stimulation in Combination with Gustatory Stimuli", Chem. Senses, 2009, pp. 499-502, vol. 34.
MacQueen et al., "Which Commercial Thickening Agent Do Patients Prefer?", Dysphagia, 2003, pp. 46-52, vol. 18.
Matta et a., "Sensory Characteristics of Beverages Prepared with Commercial Thickeners Used for Dysphagia Diets", Journal of the American Dietetic Association, 2006, pp. 1049-1054, vol. 106, No. 7.
Palmer et al., "Effects of a Sour Bolus on the Intramuscular Electromyographic (EMG) Activity of Muscles in the Submental Region, Dysphagia, 2005, pp. 210-217, vol. 20.
Pelletier, "A Comparison of Consistency and Taste of Five Commercial Thickeners", Dysphagia, 1997, pp. 74-78, vol. 12.
Pelletier et al., "Effect of Citric Acid and Citric Acid-Sucrose Mixtures on Swallowing in Neurogenic Oropharyngeal Dyshagia", Dysphagia, 2003, pp. 231-241, vol. 18.
Sciortino et al., "Effects of Mechanical, Cold, Gustatory, and Combined Stimulation to the Human Anterior Faucial Pillars", Dysphagia, 2003, pp. 16-26, vol. 18.
Hembree et al: "Dysphagia evaluation and treatment", Operative Techniques in Otolaryngology—Head and Neck Surgery, vol. 8, No. 4, Dec. 1, 1997, pp. 185-190; XP005156498.
Lacau St Guily J et al: "Troubles de la deglutition de l'adulte. Prise en charge diagnostique et therapeutique", EMC—Oto-Rhino-Laryngologie, Editions Scientifiques Et Medicales Elsevier, vol. 2, No. 1, Feb. 1, 2005, pp. 1-25; XP025361846.
PCT International Search Report for Application No. PCT/US2009/066972 with an International Filing Date of Dec. 7, 2009 and a Mailing Date of Mar. 4, 2010—5 Pages.

* cited by examiner

*Primary Examiner* — Bill Thomson
*Assistant Examiner* — Marie Archer
(74) *Attorney, Agent, or Firm* — K&L Gates LLP

(57) ABSTRACT

Methods for evaluating and treating patients for dysphagia are provided. In a general embodiment, the method comprises screening the patient for dysphagia symptoms, diagnosing and categorizing the dysphagia if the patient exceeds a threshold of dysphagia symptoms, choosing the proper dysphagia treatment product based the patient's dysphagia, and giving the patient preparation instructions for the dysphagia treatment product.

12 Claims, 3 Drawing Sheets

Dysphagia Screening Tool

| Last name: | First name: | Date: |
|---|---|---|
| Age: | I.D. Number: | |

*Observe the patient and ask if he or she has recent history (within the past month) of any of the following screening variables:*
*Complete the screen by checking the boxes that produce a 'yes' response. Assign one point for each checked box and add up the number of points to determine the screening score*

Variables identified by chart review within physician or nurse documentation

History of dysphagia? ☐

Difficulty swallowing solids? ☐

Age 70y or over? ☐

Observed variables

Facial of tongue weaknes? ☐

Change in voice quality? ☐

Self-reported variables

Facial of tongue weaknes? ☐

Drooling of liquids? ☐

Change in voice quality? ☐

Drooling of solids? ☐

Prolonged eating time? ☐

Screening score (max 10 points) ☐☐
5 points or greater 80-85% liklihood of dysphagia a risk - refer patient for dysphagia evaluation
3 points or greater 40-50% liklihood of dysphagia a risk - consider referring patient for dysphagia evaluation to enable the early management of dysphagia

FIG. 2

METHODS, SYSTEM AND KIT FOR DIAGNOSING AND TREATING DYSPHAGIA

BACKGROUND

The present disclosure is directed to medical diagnostics and treatments. More specifically, the present disclosure is directed to methods of diagnosing and treating dysphagia.

Dysphagia is the medical term for the symptom of difficulty in swallowing. Epidemiological studies estimate a prevalence rate of 16% to 22% among individuals over 50 years of age.

Esophageal dysphagia affects a large number of individuals of all ages, but is generally treatable with medications and is considered a less serious form of dysphagia. Esophageal dysphagia is often a consequence of mucosal, mediastinal, or neuromuscular diseases. Mucosal (intrinsic) diseases narrow the lumen through inflammation, fibrosis, or neoplasia associated with various conditions (e.g. peptic stricture secondary to gastroesophageal reflux disease, esophageal rings and webs [e.g. sideropenic dysphagia or Plummer-Vinson syndrome], esophageal tumors, chemical injury [e.g., caustic ingestion, pill esophagitis, sclerotherapy for varices], radiation injury, infectious esophagitis, and eosinophilic esophagitis). Mediastinal (extrinsic) diseases obstruct the esophagus by direct invasion or through lymph node enlargement associated with various conditions (tumors [e.g., lung cancer, lymphoma], infections [e.g., tuberculosis, histoplasmosis], and cardiovascular [dilated auricula and vascular compression]). Neuromuscular diseases may affect the esophageal smooth muscle and its innervation, disrupting peristalsis or lower esophageal sphincter relaxation, or both, commonly associated with various conditions (achalasia [both idiopathic and associated with Chagas disease], scleroderma, other motility disorders, and a consequence of surgery [i.e., after fundoplication and antireflux interventions]). It is also common for individuals with intraluminal foreign bodies to experience acute esophageal dysphagia.

Oral pharyngeal dysphagia, on the other hand, is a very serious condition and is generally not treatable with medication. Oral pharyngeal dysphagia also affects individuals of all ages, but is more prevalent in older individuals. Worldwide, oral pharyngeal dysphagia affects approximately 22 million people over the age of 50. Oral pharyngeal dysphagia is often a consequence of an acute event, such as a stroke, brain injury, or surgery for oral or throat cancer. In addition, radiotherapy and chemotherapy may weaken the muscles and degrade the nerves associated with the physiology and nervous innervation of the swallow reflex. It is also common for individuals with progressive neuromuscular diseases, such as Parkinson's Disease, to experience increasing difficulty in swallowing initiation. Representative causes of oropharyngeal dysphagia include those associated neurological illnesses (brainstem tumors, head trauma, stroke, cerebral palsy, Guillain-Barre syndrome, Huntington's disease, multiple sclerosis, polio, post-polio syndrome, metabolic encephalopathies, amyotrophic lateral sclerosis, Parkinson's disease, dementia), infectious illnesses (diphtheria, botulism, Lyme disease, syphilis, mucositis [herpetic, cytomegalovirus, candida, etc.]), autoimmune illnesses (lupus, scleroderma, Sjogren's syndrome), metabolic illnesses (amyloidosis, cushing's syndrome, thyrotoxicosis, Wilson's disease), myopathic illnesses (connective tissue disease, dermatomyositis, myasthenia gravis, myotonic dystrophy, oculopharyngeal dystrophy, polymyositis, sarcoidosis, paraneoplastic syndromes, inflammatory myopathy), iatrogenic illnesses (medication side effects [e.g., chemotherapy, neuroleptics, etc.], post surgical muscular or neurogenic, radiation therapy, corrosive [pill injury, intentional]), Tardive Dyskinesia [A chronic disorder of the nervous system characterized by involuntary jerky movements of the face, tongue, jaws, trunk, and limbs, usually developing as a late side effect of prolonged treatment with antipsychotic drugs], and structural illnesses (cricopharyngeal bar, Zenker's diverticulum, cervical webs, oropharyngeal tumors, osteophytes and skeletal abnormalities, congenital [cleft palate, diverticulae, pouches, etc.]).

Dysphagia is not generally diagnosed although the disease has major consequences on patient health and healthcare costs. Individuals with more severe dysphagia generally experience a sensation of impaired passage of food from the mouth to the stomach, occurring immediately after swallowing. Among community dwelling individuals, perceived symptoms may bring patients to see a doctor. Among institutionalized individuals, health care practitioners may observe symptoms or hear comments from the patient or his/her family member suggestive of swallowing impairment and recommend the patient be evaluated by a specialist. As the general awareness of swallowing impairments is low among front-line practitioners, dysphagia often goes undiagnosed and untreated. Yet, through referral to a swallowing specialist (e.g., speech language pathologist), a patient can be clinically evaluated and dysphagia diagnosis can be determined.

The general awareness of swallowing impairments is low among front-line practitioners. Many people (especially those who are elderly) suffer with undiagnosed and untreated swallowing impairments. One reason is that front-line community care practitioners (e.g., general practitioners/geriatricians, home care nurses, physical therapists, etc.) do not typically screen for the condition. If they are aware of the severity of swallowing impairments, they commonly do not use an evidence-based method of screening. Furthermore, office-based assessment of dysphagia rarely occurs.

Severity of dysphagia may vary from: (i) minimal (perceived) difficulty in safely swallowing foods and liquids, (ii) an inability to swallow without significant risk for aspiration or choking, and (iii) a complete inability to swallow. Many people with swallowing impairment do not seek medical care when symptoms are mild or unrecognized. For example, "silent aspiration," a common condition among elderly, refers to the aspiration of the oropharyngeal contents during sleep. People may compensate for less-severe swallowing impairments by self-limiting the diet. The aging process itself, coupled with chronic diseases such as hypertension or osteoarthritis, predisposes elderly to (subclinical) dysphagia that may go undiagnosed and untreated until a clinical complication such as pneumonia, dehydration, malnutrition (and related complications) occurs. Yet, the differential diagnosis of 'aspiration pneumonia' is not necessarily indicated as a result of current care practices.

The economic costs of dysphagia are associated with hospitalization, re-hospitalization, loss of reimbursement due to pay for performance ("P4P"), infections, rehabilitation, loss of work time, clinic visits, use of pharmaceuticals, labor, care taker time, childcare costs, quality of life, increased need for skilled care. Dysphagia and aspiration impact quality of life, morbidity and mortality. Twelve-month mortality is high (45%) among individuals in institutional care who have dysphagia and aspiration. The economic burden of the clinical consequences arising from lack of diagnosis and early management of dysphagia are significant.

Pneumonia is a common clinical consequence of dysphagia. The condition often requires acute hospitalization and emergency room visits. Among those that develop pneumonia due to aspiration, the differential diagnosis of 'aspiration pneumonia' is not necessarily indicated as a result of current care practices. Based on US healthcare utilization surveys from recent years, pneumonia accounted for over one million hospital admissions and an additional 392,000 were attributable to aspiration pneumonia. Individuals who have general pneumonia as the principal diagnosis have a mean 6 day hospital length of stay and incur over $18,000 in costs for hospital care. It is expected that aspiration pneumonia would carry higher costs for hospital care, based on a mean 8 day length of hospital stay. Pneumonia is life threatening among persons with dysphagia, the odds of death within 3 months is ~50% (van der Steen et al 2002). In addition, an acute insult such as pneumonia often initiates the downward spiral in health among elderly. An insult is associated with poor food/beverage intakes and inactivity, resulting in malnutrition, functional decline, and frailty. Specific interventions (e.g. to promote oral health, help restore normal swallow, or reinforce a swallow-safe bolus) would benefit persons at risk for (due to aspiration of oropharyngeal contents, including silent aspiration) or experiencing recurrent pneumonia.

Similar to pneumonia, dehydration is a life-threatening clinical complication of dysphagia. Dehydration is a common co-morbidity among hospitalized individuals with neurodegenerative diseases (thus, likely to have a swallowing impairment). The conditions of Alzheimer's disease, Parkinson's disease, and multiple sclerosis account for nearly 400,000 US hospital discharges annually, and up to 15% of these patients suffer dehydration. Having dehydration as the principal diagnosis is associated with a mean 4 day length of hospital stay and over $11,000 in costs for hospital care. Nevertheless, dehydration is an avoidable clinical complication of dysphagia.

Malnutrition and related complications (e.g., [urinary tract] infections, pressure ulcers, increased severity of dysphagia [need for more-restricted food options, tube feeding, and/or percutaneous endoscopic gastrostomy (PEG) placement and reduced quality of life], dehydration, functional decline and related consequences [falls, dementia, frailty, loss of mobility, and loss of autonomy]) can arise when swallowing impairment leads to fear of choking on food and liquids, slowed rate of consumption, and self-limited food choices. If uncorrected, inadequate nutritional intake exacerbates dysphagia as the muscles that help facilitate normal swallow weaken as physiological reserves are depleted. Malnutrition is associated with having a more than 3-times greater risk of infection. Infections are common in individuals with neurodegenerative diseases (thus, likely to have a chronic swallowing impairment that jeopardizes dietary adequacy). The conditions of Alzheimer's disease, Parkinson's disease, and multiple sclerosis account for nearly 400,000 US hospital admissions annually, and up to 32% of these patients suffer urinary tract infection.

Malnutrition has serious implications for patient recovery. Malnourished patients have longer length of hospital stay, are more likely to be re-hospitalized, and have higher costs for hospital care. Having malnutrition as the principal diagnosis is associated with a mean 8 day length of hospital stay and nearly $22,000 in costs for hospital care. Furthermore, malnutrition leads to unintentional loss of weight and predominant loss of muscle and strength, ultimately impairing mobility and the ability to care for oneself. With the loss of functionality, caregiver burden becomes generally more severe, necessitating informal caregivers, then formal caregivers, and then institutionalization. However, malnutrition is an avoidable clinical complication of dysphagia.

Among persons with neurodegenerative conditions (e.g., Alzheimer's disease), unintentional weight loss (a marker of malnutrition) precedes cognitive decline. In addition, physical activity can help stabilize cognitive health. Thus, it is important to ensure nutritional adequacy among persons with neurodegenerative conditions to help them have the strength and endurance to participate in regular therapeutic exercise and guard against unintentional weight loss, muscle wasting, loss of physical and cognitive functionality, frailty, dementia, and progressive increase in caregiver burden.

Falls and related injuries are a special concern among elderly with neurodegenerative conditions, associated with loss of functionality. Falls are the leading cause of injury deaths among older adults. Furthermore, fall-related injuries among elderly accounted for more than 1.8 M US emergency room visits in a recent year. Direct medical costs totaled $179 M for fatal and $19.3 B for nonfatal fall-related injuries in the period of a year. As an effect of an ambitious non-payment for performance initiative introduced in US hospitals in October 2008, Medicare will no longer pay hospitals for treatment cost of falls and related injuries that occur during the hospital stay. Hospitals will face a loss of ~$50,000 for each elderly patient who falls and suffers hip fracture while in hospital care. This new quality initiative is based on the premise that falls are an avoidable medical error. In other words, falls are preventable within reason by applying evidence-based practices including medical nutrition therapy as nutritional interventions are efficacious in the prevention of falls and related injuries (e.g., fractures) among elderly.

Chewing and swallowing difficulties are also recognized risk factors for pressure ulcer development. Pressure ulcers are considered an avoidable medical error, preventable within reason by applying evidence-based practices (including nutritional care, as pressure ulcers are more likely when nutrition is inadequate). Pressure ulcers are a significant burden to the health care system. In US hospitals in 2006, there were 322,946 cases of medical error connected with pressure ulcer development.

The average cost of healing pressure ulcers depends on the stage, ranging from ~$1,100 (for stage II) to ~$10,000 (for stage III & IV pressure ulcers). Thus, the estimated cost of healing the cases of medical error connected with pressure ulcer development in one year, is in the range of $323 M to $3.2 B. As an effect of an ambitious non-payment for performance initiative introduced in US hospitals in October 2008, Medicare will no longer pay hospitals for treatment cost of pressure ulcers that develop during the hospital stay (up to $3.2 B annually). Pressure ulcers are preventable within reason, in part, by assuring nutritional intakes are adequate. Furthermore, specific interventions including the use of specialized nutritional supplements help reduce the expected time to heal pressure ulcers once they've developed.

In the US long-term care facilities, quality of care standards are enforced via the frequent regulatory survey. Surveyors will consider facilities out of compliance when they uncover evidence of actual or potential harm/negative outcomes. The range of penalties includes fines, forced closure, as well as lawsuits and settlement fees. The Tag F325 (nutrition) survey considers significant unplanned weight change, inadequate food/fluid intake, impairment of anticipated wound healing, failure to provide a therapeutic diet as ordered, functional decline, and fluid/electrolyte imbalance as evidence for providing sub-standard [Nutrition] care. The Tag F314 (pressure ulcers) survey mandates that the facility must ensure that a resident who is admitted without pressure ulcers does not develop pressure ulcers unless deemed unavoidable. In addition, The Tag F314 survey mandates that a resident having pressure ulcers receives necessary treatment and services to promote healing, prevent infection and prevent new pressure ulcers from developing.

Considering current care practices, a large discrepancy exists in the management of dysphagia. A standardized approach to dysphagia patient care that incorporated evidence-based methods would improve the lives of a large and growing number of persons with swallowing impairments. Specific interventions (e.g. to promote oral health, help restore normal swallow, or reinforce a swallow-safe bolus) can enable persons to eat orally (vs. being tube fed and/or requiring PEG placement) and experience the psycho-social aspects of food associated with general well being while guarding against the clinical complications that arise from lack of diagnosis and appropriate early management of dysphagia.

SUMMARY

The present disclosure relates to methods for diagnosing, evaluating and treating patients for dysphagia and for generating revenue from same. By evaluating and treating patients for dysphagia, subsequent health problems can be prevented or mitigated. In a general embodiment, the method comprises screening the patient for dysphagia symptoms, diagnosing and categorizing the dysphagia if the patient exceeds a threshold of dysphagia symptoms, choosing the proper dysphagia treatment product based the patient's dysphagia, and giving the patient preparation instructions for the dysphagia treatment product. The screening step can comprise having the patient answer questions from a dysphagia screening questionnaire and scoring the questionnaire based on the patient's answers.

In an embodiment, the method is performed using a computer process. For example, the screening, diagnosing, categorizing, choosing and giving treatment steps can be an algorithm implemented in a computer program.

In another embodiment, the present disclosure provides a method of treating patients for dysphagia. The method comprises screening the patient for dysphagia symptoms, diagnosing and categorizing the dysphagia if the patient exceeds a threshold of dysphagia symptoms, and providing a physical therapy regime of the patient based the patient's dysphagia. The physical therapy regime can comprise, for example, performing specific postural positioning during and after eating or performing rehabilitative exercises. The physical therapy regime can also be paired with an anabolic nutritional regime.

In an alternative embodiment, the present disclosure provides a method for providing treatment for a patient having dysphagia at a care center. The method comprises screening the patient for dysphagia symptoms, diagnosing and categorizing the dysphagia if the patient exceeds a threshold of dysphagia symptoms, and providing the patient products and services to facilitate rehabilitation of the patient at the care center.

In yet another embodiment, the present disclosure provides a method for generating revenue. The method comprises screening the patient for dysphagia symptoms, diagnosing and categorizing the dysphagia based on a score related to the dysphagia symptoms, providing the patient at least one product or service to facilitate rehabilitation of the patient at the care center, and charging the patient a fee depending on the product or the service.

In still another embodiment, the present disclosure provides a kit for providing treatment for a patient having dysphagia. The kit comprises: (i) a screening tool that screens the patient for dysphagia, (ii) a diagnostic test that categorizes the dysphagia if the patient exceeds a threshold of dysphagia symptoms, (iii) a suggested course of dysphagia treatment based the patient's dysphagia, and (iv) instructions for implementing the dysphagia treatment.

In another embodiment, the present disclosure provides a method of reducing healthcare costs associate with dysphagia. The method comprises screening the patient for dysphagia symptoms, diagnosing and categorizing the dysphagia if the patient exceeds a threshold of dysphagia symptoms, providing dysphagia treatment to the patient based on the patient's dysphagia. The dysphagia treatment can comprise a dysphagia treatment product and/or a physical therapy.

In yet another embodiment, the present disclosure provides a diagnostic screening tool comprising a questionnaire that includes past information relating to dysphagia variables identified by caretaker review, observed variables and self-reported variables. The diagnostic screening tool also comprises a screening score system to determine the likelihood of dysphagia risk.

In still another embodiment, the present disclosure provides a method diagnosing dysphagia. The method comprises having a patient answer questions from a questionnaire that includes past information relating to dysphagia variables identified by caretaker review, observed variables and self-reported variables. A score is determined for the questionaire based on the patient answers. The method further comprises identifying and categorizing the dysphagia if the patient exceeds a threshold score.

An advantage of the present disclosure is to provide a method for screening patients having dysphagia.

Another advantage of the present disclosure is to provide a method for diagnosing patients having dysphagia.

Yet another advantage of the present disclosure is to provide a method for treating patients having dysphagia.

Still another advantage of the present disclosure is to provide a method of generating revenue for treating patients having dysphagia.

Another advantage of the present disclosure is to provide a kit for treating dysphagia.

Yet another advantage of the present disclosure is to provide an dysphagia treatment care center.

Additional features and advantages are described herein, and will be apparent from the following Detailed Description and the figures.

BRIEF DESCRIPTION OF THE FIGURES

FIG. 2 shows a dysphagia screening tool questionnaire in one embodiment of the present disclosure.

DETAILED DESCRIPTION

Figure 1:
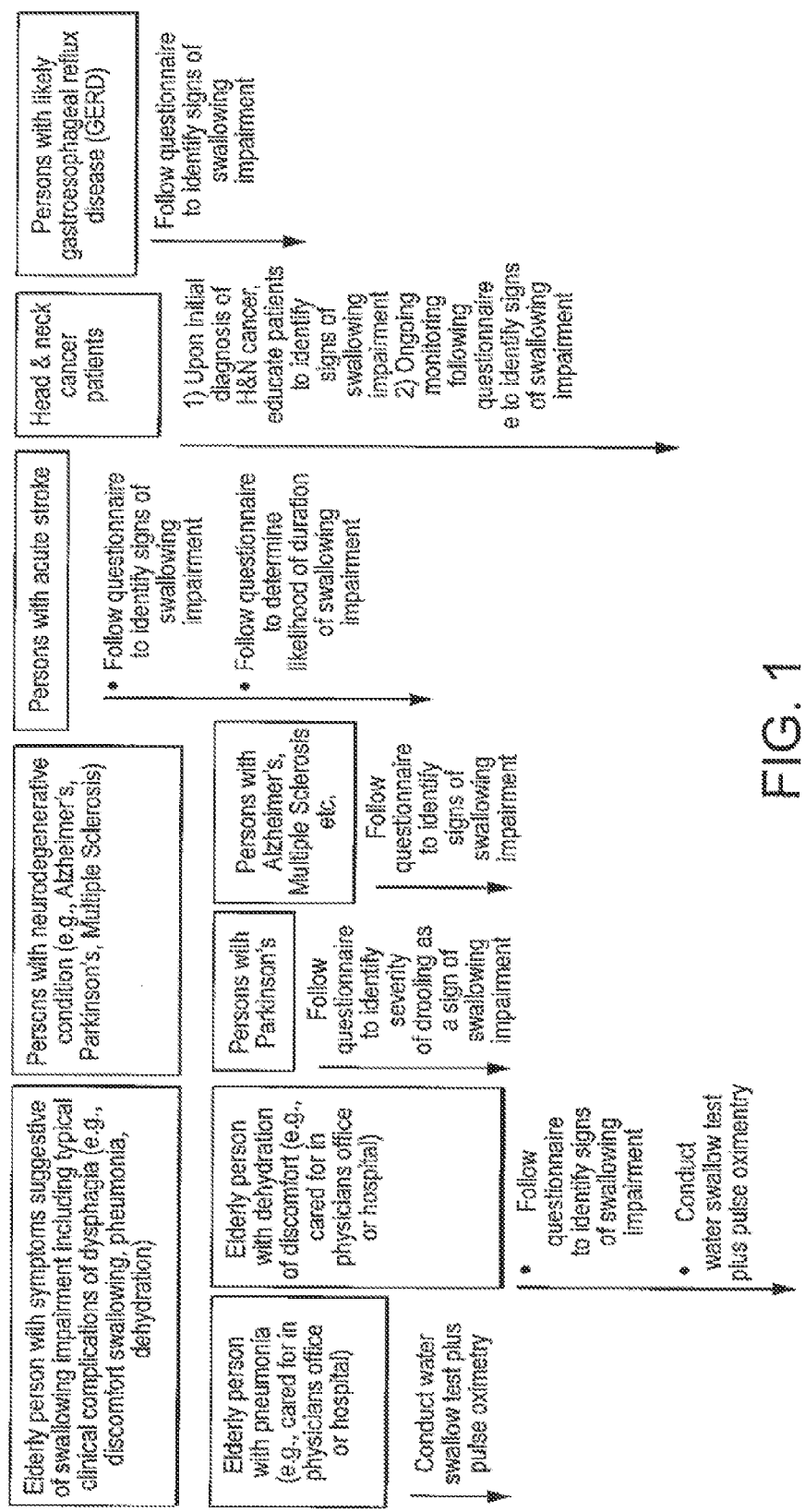
FIG. 1 shows a schematic flowchart illustrating the screening procedure for various patient types.
Figure 3:
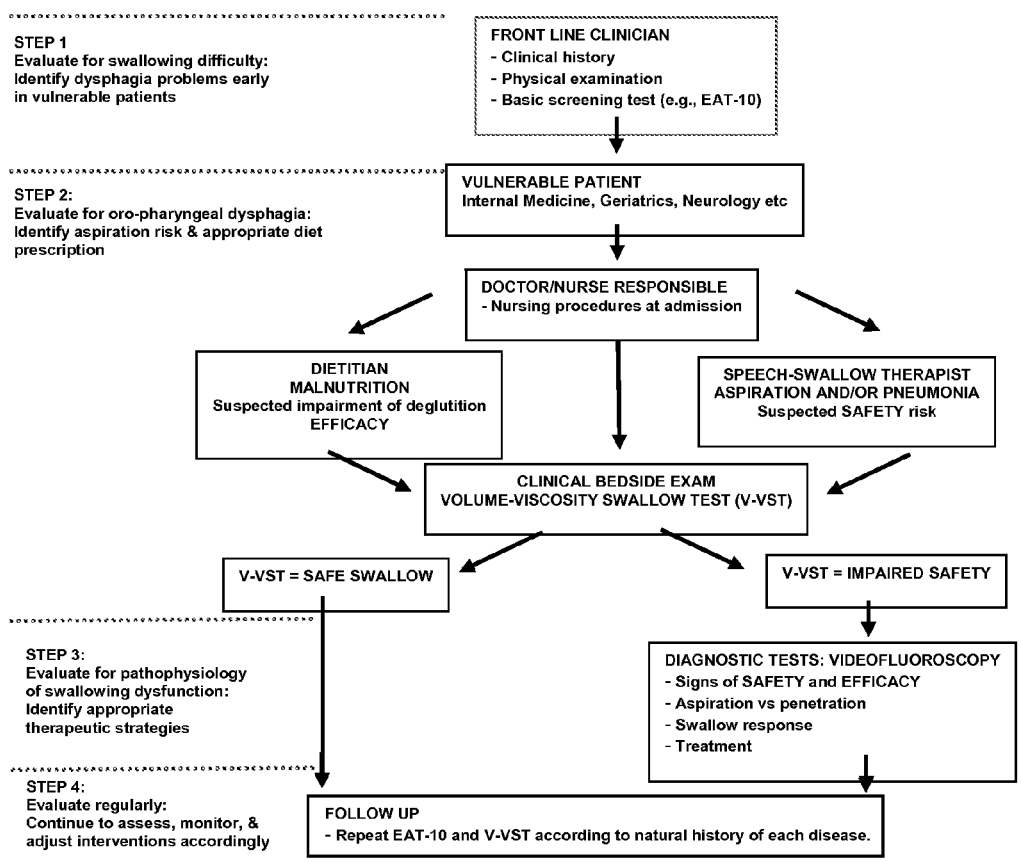
FIG. 3 shows a schematic flowchart illustrating the management of a patient with dysphagia.

The present disclosure relates to methods for diagnosing, evaluating and treating patients for dysphagia. The present disclosure also relates to methods for providing treatment for a patient having dysphagia at a care center and for generating revenue from same. In addition, the present disclosure relates to kits for evaluating and treating patients having dysphagia.

The normal swallowing of a human (or mammal) involves three distinct phases which are interdependent and well coordinated: (i) the oral, (ii) the pharyngeal, and (iii) the esophageal phases. In the oral phase, which is under voluntary control, food that has been chewed and mixed with saliva is formed into a bolus for delivery by voluntary tongue movements to the back of the mouth, into the pharynx. The pharyngeal phase is involuntary and is triggered by food/liquid bolus passing through the faucial pillars into the pharynx. Contraction of the three constrictors of the pharynx propel the bolus towards the upper esophageal sphincter. Simultaneously, the soft palate closes the nasopharynx. The larynx moves upwards to prevent food or liquid passing into the airway, which is aided by the backward tilt of the epiglottis and closure of the vocal folds. The esophageal phase is also involuntary and starts with the relaxation of the upper esophageal sphincter followed by peristalsis, which pushes the bolus down to the stomach.

Dysphagia refers to the symptom of difficulty in swallowing. The following general causes of dysphagia have been identified:
a) A decreased ability to swallow
b) Tongue not exerting enough pressure on soft palate and/or hard palate
  i) Iatrogenic
    (1) Surgical removal of part of the tongue or soft palate
      (a) Treatment for snoring or sleep apnea
      (b) Resection due to tumor (malignant or benign)
  ii) Genetic
    (1) Hypoplasia of the tongue and/or soft palate
    (2) Hypo or lack of innervation to tongue and/or soft palate
  iii) Traumatic
    (1) Tissue damage
    (2) Deinnervation/hypoinnervation
  iv) Neurologic
    (1) Local deinnervation/hypoinnervation
    (2) CNS
      (a) Post stroke
      (b) Demylination
c) Abnormal degree and timing of airway closure and behavior of the epiglottis, arytenoids, vocal folds, larynx movement
  i) Not closing and opening at proper times
    (1) Opening too early
    (2) Not closing in time
      (a) Delayed closing of one or more of the structures
  ii) Not closing completely (insufficient flexibility—atrophy)
  iii) Abnormal movement of the airway structures The consequences of untreated or poorly managed oral pharyngeal dysphagia can be severe, including dehydration, malnutrition leading to dysfunctional immune response, and reduced functionality, airway obstruction with solid foods (choking), and airway aspiration of liquids and semi-solid foods, promoting aspiration pneumonia and/or pneumonitis. Severe oral pharyngeal dysphagia may require nutrition to be supplied by tube feeding.

Mild to moderate oral pharyngeal dysphagia may require the texture of foods to be modified in order to minimize the likelihood of choking or aspiration. This may include the thickening of liquids and/or pureeing of solid foods, both of which have been shown to be the most effective means of preventing choking and aspiration during the eating process. Thickened liquids are designed to have three properties: (i) a more cohesive bolus that can be maintained throughout the action of swallowing, (ii) slower delivery to the throat, thereby compensating for the increased period in which the swallowing reflexes prepare for the thickened liquid, and (iii) provide greater density to increase awareness of the presence of food or liquid bolus in the mouth.

In a general embodiment, the present disclosure provides a method of evaluating and treating patients for dysphagia. The patients can be healthy individuals or can have medical conditions as shown in FIG. 1. The method comprises screening the patient for dysphagia symptoms, diagnosing and categorizing the dysphagia if the patient exceeds a threshold of dysphagia symptoms, choosing the proper dysphagia treatment product based the patient's dysphagia, and giving the patient preparation instructions for the dysphagia treatment product.

In another embodiment, the present disclosure provides a method of treating patients for dysphagia. The method comprises screening the patient for dysphagia symptoms, diagnosing and categorizing the dysphagia if the patient exceeds a threshold of dysphagia symptoms, and providing a physical therapy regime of the patient based the patient's dysphagia. The physical therapy regime can comprise, for example, performing specific postural positioning during and after eating or performing rehabilitative exercises. The physical therapy regime can also be paired with an anabolic nutritional regime.

The screening step in embodiments of the present disclosure can comprise having the patient answer questions from a dysphagia screening questionnaire and scoring the questionnaire based on the patient's answers. For example, a dysphagia screening tool questionnaire can be filled out by a patient healthcare provider ("HCP") (e.g. doctor, nurse, nurse's aid, or care giver), patient, family or other caregiver. A sample questionnaire is shown in FIG. 2. Answers to the questions are based on the patient's condition. Points are given based on the answers, and a percentage likelihood of dysphagia risk is determined based on the cumulative point total. The questionnaire can be a quick and easy, evidence-based method for predicting dysphagia risk that is useful in unlimited healthcare settings and even appropriate for informal caregivers to complete.

It should be appreciated that the patient can refer to a mammal, and especially a human. Mammals can include, but are not limited, to rodents, aquatic mammals, domestic animals such as dogs and cats, farm animals such as sheep, pigs, cows and horses, and humans. Wherein the term "mammal" is used, it is contemplated that it also applies to other animals that are capable of the effect exhibited or intended to be exhibited by the mammal.

As used herein, "complete nutrition" are preferably nutritional products that contain sufficient types and levels of macronutrients (protein, fats and carbohydrates) and micronutrients to be sufficient to be a sole source of nutrition for the animal to which it is being administered to.

As used herein, "effective amount" is preferably an amount that prevents a deficiency, treats a disease or medical condition in an individual or, more generally, reduces symptoms, manages progression of the diseases or provides a nutritional, physiological, or medical benefit to the individual. A treatment can be patient- or doctor-related. In addition, while the terms "individual" and "patient" are often used herein to refer to a human, the invention is not so limited. Accordingly, the terms "individual" and "patient" refer to any animal, mammal or human having or at risk for a medical condition that can benefit from the treatment.

As used herein, "incomplete nutrition" are preferably nutritional products that do not contain sufficient levels of macronutrients (protein, fats and carbohydrates) or micronutrients to be sufficient to be a sole source of nutrition for the animal to which it is being administered to.

As used herein, "Long term administrations" are preferably continuous administrations for more than 6 weeks.

The term "microorganism" is meant to include the bacterium, yeast and/or fungi, a cell growth medium with the microorganism or a cell growth medium in which microorganism was cultivated.

As used herein, a "Prebiotic" is preferably a food substances that selectively promote the growth of beneficial bacteria or inhibit the growth of pathogenic bacteria in the intestines. They are not inactivated in the stomach and/or upper intestine or absorbed in the GI tract of the person ingesting them, but they are fermented by the gastrointestinal microflora and/or by probiotics. Prebiotics are for example defined by Glenn R. Gibson and Marcel B. Roberfroid, Dietary Modulation of the Human Colonic Microbiota: Introducing the Concept of Prebiotics, J. Nutr. 1995 125: 1401-1412.

As used herein, Probiotics micro-organisms (hereinafter "probiotics") are preferably microorganisms (alive, including semi-viable or weakened, and/or non-replicating or dead), metabolites, microbial cell preparations or components of microbial cells that could confer health benefits on the host when administered in adequate amounts, more specifically, that beneficially affect a host by improving its intestinal microbial balance, leading to effects on the health or well-being of the host. (Salminen S, Ouwehand A. Benno Y. et al "Probiotics: how should they be defined" Trends Food Sci. Technol. 1999:10 107-10). In general, it is believed that these micro-organisms inhibit or influence the growth and/or metabolism of pathogenic bacteria in the intestinal tract. The probiotics may also activate the immune function of the host. For this reason, there have been many different approaches to include probiotics into food products.

As used herein, "Short term administrations" are preferably continuous administrations for less than 6 weeks.

As used herein, the terms "treatment", "treat" and "to alleviate" is preferably to both prophylactic or preventive treatment (that prevent and/or slow the development of a targeted pathologic condition or disorder) and curative, theraputic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The terms "treatment" and "treat" also refer to the maintenance and/or promotion of health in an individual not suffering from a disease but who may be susceptible to the development of an unhealthy condition, such as nitrogen imbalance or muscle loss. The terms "treatment", "treat" and "to alleviate" are also intended to include the potentiation or otherwise enhancement of one or more primary prophylactic or therapeutic measure.

As used herein, a "tube feed" is preferably a complete or incomplete nutritional products that are administered to an animal's gastrointestinal system, other than through oral administration, including but not limited to a nasogastric tube, orogastric tube, gastric tube, jejunostomy tube (J-tube), percutaneous endoscopic gastrostomy (PEG), port, such as a chest wall port that provides access to the stomach, jejunum and other suitable access ports.

As used herein, "Comensal bacteria" are those microorganisms that help the digestion of food and acquiring of nutrients such as vitamins B and K, and assisting the immune system in preventing the colonization of pathogens that cause disease by competing with them.

As used herein, a "Comensal Effect" is when a microorganism, by itself, or aids another organism, in helping the digestion of food and acquiring of nutrients such as vitamins B and K, and assisting the immune system in preventing the colonization of pathogens that cause disease by competing with them.

All dosage ranges contained within this application are intended to include all numbers, whole or fractions, contained within said range.

If the patient exceeds a threshold of dysphagia symptoms according to the questionnaire (e.g. based on the final score), further diagnosing and categorizing the dysphagia of the patient can be done by one or more of the following techniques:

a. Measuring force exerted by tongue on soft and/or hard palate
  i. Can be assessed by testing the strength of the tongue by determining the ability of an individual to exert a threshold force on the soft and/or hard palate (e.g., if the patient can break tongue depressors of specific tensile strength).
b. Determining the degree and timing of airway closure including whether the epiglottis is closing completely
  i. Can be assessed by instrumental procedure (e.g. videofluoroscopic swallow study ("VFSS") or fiberoptic endoscopic evaluation of swallowing ("FEES") procedure) to determine physiological functions of swallow that enables differential diagnosis of dysphagia and suggest suitable dietary modifications.
c. Determining if the airway closure including epiglottis timing is correct
  i. Can be assessed by instrumental procedure (VFSS or FEES) to determine physiological functions of swallow that enables differential diagnosis of dysphagia and suggest suitable dietary modifications.
  ii. Corn Flake Test (discussed in example section)
d. At-home 24-hour tracheal pH monitoring
  i. Characterizes what occurs in real-life. Compared to the VFSS that offers a 'short film' of the patient's swallowing capabilities in an unnatural environment, the 24-h tracheal pH monitoring offers a 'mini-series' view of the patient's swallowing ability, including the ability to observe an individual in their natural environment and detect silent aspiration (including that during sleep).
  ii. The patient is instructed to consume standardized dysphagia care products at specific times, while maintaining a patient diary of the time of consumption, product consumed, body position during and after consumption, comfort level, and potential events (e.g. choking during swallow).
  iii. Though health information technology, the tracheal pH monitoring system offers real-time results on the incidence of aspiration that can be viewed by the HCP, and can help practitioners identify dietary modification consistencies that are inside and outside of the individual's swallow-safe bolus capacity.
  iv. This method of identifying suitable dietary modifications facilitates individualized intervention strategies, identifies appropriate compensatory interventions, enables the person to resume eating as normal as possible while also helping to guard against the clinical complications of dysphagia.
e. Ultrasound to detect abnormal oropharyngeal motor function and suggest appropriate rehabilitative exercises & therapies (e.g., anabolic nutrition)
f. Deploy preparation tool
  i. Spread Line Test ("SLT")—Tool that measures the distance liquid flows over a flat surface.

ii. Evidence based: statistically correlates with viscometer iii. Cheap and easy to use, at home and at institutions g. Oral health assessment i. Microbiological assessment of a swab from the oral cavity to determine the need for oral health intervention The following specialized dysphagia treatments can be used to compensate for specific swallowing impairment(s) based on the diagnosis/categorization results:

a. Specific postural positioning during and after eating b. Rehabilitative exercises (e.g., pharyngeal squeeze) that may be paired with anabolic nutrition for optimal benefits c. Oral health interventions d. Compositions to enhance/restore immunity (e.g. lacto-wolfberry)

e. Composition(s) to trigger/enhance/restore the swallowing reflex (e.g., from dietary (e.g., naturally-occurring) and/or synthetic sources).

f. Compositions to enhance/restore mucosa (e.g., TGF-β for persons with head & neck cancer)

g. Compositions to support functionality and help guard against falls, frailty, cognitive decline, and loss of mobility & autonomy h. Dietary modification in accordance with standardized specifications In the management of a patient with impaired swallowing, different treatment strategies are necessary depending on the pathophysiology of the patient's oral and pharyngeal dysfunction. A major problem is patients who suffer from oral and/or pharyngeal impairment leading to misdirected swallowing and/or residue of bolus material. The pharyngeal dysfunction can also lead to insufficient intake of calories and thereby to malnutrition. Defective intake of fluid may cause dehydration. The best treatments of such dysfunction are head positioning, swallowing maneuvers and/or diet modification. However, due to a more global neurological disease that impairs cognitive capacity and speech, dysphagic patients often have problems understanding and following instruction concerning swallowing maneuvers. Many patients are also too fatigued to participate in swallowing therapy. For those patients, diet modification is essential.

In order to enhance safety and progress in persons with oropharyngeal dysphagia, it is important that the recommended liquid consistency is well adapted to the patient disorder and consistently produced. Well controlled rheological properties of the thickened liquids are a must. However for the patient, the perception of the thickened liquids may be as important as their physical properties for two main reasons: 1) an acceptable taste is important to maximize compliances with the recommended diet, 2) Sensory perception could help in triggering swallowing.

1) Acceptable Taste to Maximize Compliances:

Few articles on sensory characterization of commercial thickeners used for dysphagia diets are published (Pelletier et al, 1997, Lotong et al., 2003, Matta et al., 2006). Pelletier et al. (1997) evaluated the performance of five commercial thickeners (Thick It, Thicken Right, Thick and Easy, Thicken up and QuikThick). The findings suggested that no one of commercial thickeners produces a desired consistency and was consistently superior regarding taste. To enhance taste in thickened liquids, the authors recommended using flavorings. Matta et al. (2006) also reported that with thickeners, the main flavors of base beverages (milk, apple juice and orange juice) were suppressed and imparted slight off-flavors (bitter, sour, metallic or astringent). Starch based thickeners (Thick and Easy, Thicken up) imparted a starchy flavor and grainy texture, whereas gum based thickeners (Thick and Clear and Simply Thick) gave added slickness to the beverages. The authors concluded that additional development of thickening agents seems necessary for improved sensory properties. Furthermore, the hedonic aspect (likes or dislikes) could play an important role for two reasons:

1) Patients who have a strong dislike of thickened liquids may, as a result, be less compliant and drink less, possibly contributing to other complications, such as dehydration and malnutrition. A survey carried out in 2005 on practice patterns of Speech language pathologists (Garcia et al., 2005) showed that most practitioners perceived that their patients disliked thickened liquids. Overall, patients' dislike seemed to be related to the degree of thickness. The nectar consistency is the most well-tolerated level of modification for patients requiring thickened liquids. Few articles are published on palatability of commercial thickened liquids (Garcia et al., 2005, Pulver et al., 1999, Macqueen et al., 2003) however only one (Macqueen et al., 2003) reports liking of dysphagic patients instead of SLP perception of patient's liking, which may be different. Modified food texture, viscosity, and nutrient content may improve safety and nutrition of the dysphagic patients but not if they don't accept the diet. By offering more palatable thickening agents, we could improve compliance with speech and language therapy recommendations, thereby reducing the patients' risk of aspiration. Indeed, based on a retrospective cohort study of 140 patients who had videofluoroscopic studies, Low et al. (2001) showed that non-compliance with recommendations about dysphagia management is associated with adverse outcomes such as high mortality rate and aspiration pneumonia.

2) Food hedonics could influence swallowing physiology. Leow et al. (2007) hypothesised that sweet solutions could be swallowed quicker due to its high hedonic value but they also hypothesised that bitter foods, said to have a low hedonic tone coupled with the tendency toward avoidance or even expectoration, may also lead to abbreviated swallowing times.

An evaluation of the ease of swallowing of four food samples based on mango puree, with no or added barium sulphate medium was recently published (Ekberg et al., 2009). They found that the ease of swallowing was significantly higher in the samples without added contrast medium. Samples with high concentration of barium sulphate were perceived thicker and with high amount of particles, which probably explains why these samples were perceived as less easy to swallow. The perception of a safe and easy to swallow bolus may be as important as it physical safety.

Sensory Triggers of Swallowing:

The aspect of sensory triggering of swallowing might be even more interesting for development of dysphagia products. Several articles are claiming that a sour bolus improves swallowing in neurogenic dysphagia. The hypothesis given on the impact of taste on swallowing function is that "taste is an important oral sensory stimulus, . . . that . . . might . . . increase the preswallow sensory input to the cortex and brain stem, thus lowering the swallow threshold. Lowering the swallowing threshold might reduce the oral onset time of swallow (i.e, the time from command to swallow until onset of oral transit) and improve triggering of the pharyngeal swallow in patients with neurogenic dysphagia" (Logemann et al., 1995). In the Logeman's study, videofluorographic evaluations (VFSS) were carried out using either 50% water/ 50% E-Z-M barium sulphate solution or 50% Real Lemon Juice/50% E-Z-M barium sulphate solution. Dysphagic patients revealed significantly improved onset of the oral swallow in response to the sour bolus as compared to the non-sour bolus. The subjects who had suffered from a stroke exhibited a number of other improvements in the swallow as a result of the sour bolus, including reduced oral transit time and pharyngeal transit time, and improved oropharyngeal swallow efficiency. Some patients also exhibited reduced aspiration as a result of the sour bolus. In no case did the sour bolus significantly worsen the oropharyngeal swallow measure. Logemann et al. (1995) also hypothesised that the sour bolus may rapidly increase salivation that may help in the swallowing. Pelletier et al. (2003) confirmed the observations made by Logeman et al. (1995). They tested 2.7% citric acid (concentration estimated to be isosour to the acid level presented in Logeman et al.'s study) on another group of neurogenic dysphagic patients using fiberoptic endoscope (FEES) instead of VFFS. Citric acid (2.7%) significantly reduced aspiration and penetration compared with water. Furthermore, subjects showed significantly increased spontaneous dry swallows in response to citric acid stimuli. Pelletier et al. (2003) suggested that the effect of citric acid on swallowing function could be due to the trigeminal stimulation of the citric acid.

Other studies on the effect of sour bolus on swallowing were also carried out on healthy subjects. Using intramuscular EMG, Ding et al. (2003) and Palmer et al. (2005) reported stronger muscle contraction of submental muscles when sour boluses were used compared to water boluses. Palmer et al. (2005) observed that activation of the myolohyoid, anterior belly of the digastric and geniohyoid muscles was more closely timed during a sour bolus. A sour bolus may invigorate the oral muscles resulting in stronger and quicker contractions during the swallowing. The authors argued that "It is likely that the changes in videofluoroscopic events, such as rapid transit times noted in Logemann et al.'s study were, at least in part, the results of quicker and more tightly activated muscles activity from the increased oropharyngeal sensory stimulation". The stronger submental muscle contraction in presence of sour bolus was confirmed by Leow et al. (2007). The authors postulated that "sensory characteristics of citric acid used in this study was sufficient to increase nucleus tractus solitarius (NTC) activation, which lead to a increase in the nucleus ambiguous (NA) motor activation resulting in greater muscle contraction." However, Hamdy et al. (2003) found the opposite effects of sour bolus in their healthy and stroke population. Instead of facilitating swallows, liquid cold sour boluses decrease the capacity and speed of swallow. They performed a water swallow test (SWT), which consists in asking subject to drink the contents in one cup as quickly and as comfortably as possible whilst being precisely timed. One difference between Hamdy and the other studies is the volume of liquid: 50 ml was given in Hamdy study instead of much smaller volumes in the other studies (from 1 to 3 ml). The volume of the bolus given to the patients may have played an important role.

Comments from Sciortino et al. (2003) let suppose a scientific gap in this field: "Much of what we know about chemosensitive regions important for evoking the swallow response has come from animal search. Similar research in human subjects is sparse". Using surface electromyography (sEMG), Ding et al. (2003) found stronger submental muscle contraction for salty boluses and significant shorter submental EMG start time for salty, sweet and sour solutions compared to water. Infrahyoid EMG start time was also found significantly shorter in the sweet and sour taste conditions. The contribution of the shortened start time to swallowing is difficult to attribute because submental muscle can be involved either in oral and pharyngeal phases of swallow. However, from these results, the authors concluded that "taste receptors seems to be able to partially affect the sequence of events in swallowing". Ding et al. (2003) also investigated the combined effect of consistency (cottage cheese) and taste on submental and infrahyoid start time. They showed that the effect of taste was even more prominent. Pelletier et al. (2006) showed that moderate sucrose, high salt and high citric acid elicited significantly high lingual swallowing pressures compared with the pressures generated by water, which may help in swallowing. No effect was found with bitter solution. Leow et al. (2007) also investigated the influence of taste on swallowing apnea, oral preparation time and duration, and amplitude of submental muscle contraction thanks to respiratory airflow and sEMG methods. Contrary to other studies, gelled matrices were used. The authors argued that gelled matrices may prolong stimulation of peripheral sensory receptors compared with liquid boluses. No significant influence of taste on the phase location of swallowing apnea was found. However, significant taste effects for oral preparation time, submental sEMG amplitude and duration were found. Sour and sweet tastants had the shortest oral bolus preparation time and the shorter duration of submental sEMG contraction time when compared with bitter and salty tastants. There were no significant differences in oral preparation time for neutral, salty and bitter tastants when compared with each other. Bitter tastants showed significantly longer submental sEMG time compared to all the other tastants. The authors suggested that this prolongation in oral preparation may facilitate swallowing.

However, one article from Chee et al. (2005) reported that glucose, citrus, saline and quinine solutions has no effect on swallowing capacity and decrease swallowing speed, when compared with water using the swallowing water test (SWT). However, the authors recognized that "taste and other sensory stimuli, by activating sensory receptors, are likely to provide significant inputs to the NTS and higher centers in regulating swallowing capacity". To explain their results, the authors argued that "the heightened sensory input may have been perceived as an uncharacteristically intense stimulus and such stimuli may have altered behavior either by causing the subject to attend more carefully to the task or though a conscious increase perception of the bolus. The resultant effect may be the elicitation of a protective mechanism that reduces the rate of ingested bolus". However, the concentrations used in this study are not higher than the ones used in previous studies, but once again the bolus volume was much bigger in this study (50 ml) than in the previous studies (5 to 10 ml). Kaatzke-McDonald et al. (1996) did not observed significant difference among glucose, saline and distilled water with respect to the latency of evoked swallowing. Salty solutions were slightly more effective than distilled water in the number of swallowing evoked but the changes was very small. Taste solutions were infused for 3 seconds through a 1.2 mm diameter intraoral tube by a pump at a rate of 0.1 ml/sec to minimize mechanical effect of the stimulus. Swallowing latency and frequency was measured thanks to a laryngograph. The difference in methodology (infusion instead of consumption) may have influenced the result. The authors recognized that they data apply specifically to the faucial pillar area and it may be that cold fluids in greater quantities are more effective.

Both high salt and high citric acid are known to elicit chemesthesis mediated by the trigeminal nerve; therefore, Pelletier et al. (2003) suggested that "chemesthesis may play a crucial role in swallowing physiology. If true, dysphagia diet recommendation that include trigeminal irritants such as carbonation may be beneficial to individuals with Dysphagia." Results from Bulow M. et al. (2003) are in accordance with Pelletier et al.'s hypotheses. They showed during a therapeutic videoradiographic swallowing examination that carbonated liquid, known as a trigeminal stimulation, reduced the penetration/aspiration to the airways and the pharyngeal transit time. Pharyngeal retention was also significantly reduced. The authors explained these results by the stimulating effect of molecules from the carbonic acid on the receptors at the faucial isthmus in the mouth: "It may evoke more afferent impulses (sensory input) to the solitary tract nucleus in the medulla oblongata in the brain stem, eliciting the pharyngeal swallow more rapidly". The authors concluded that "carbonated liquids are a valuable treatment option for patients with penetration/aspiration".

A very recent paper (Welge-Lussen et al., 2009) also suggests that retronasal olfactory stimulation using a food like odorant, vanillin, in combination with a congruent sweet taste facilitates swallowing in terms of both the frequency of swallows and the latency of the first swallow following odorant stimulus. Ultrasound recording of the mouth floor was used to document swallowing. This study was only carried out on one flavour with healthy subjects. The authors recognised that further investigations to examine the influence of odor quality, hedonics and familiarity on swallowing are needed.

Thermal tactile stimulation therapy also let suppose the influence of sensory perception in swallowing. It has for a long time been used as a specific technique to treat delayed pharyngeal swallow. Its purpose according to Logemann (1986) "is to heighten the sensitivity for the swallow in the oral cavity so that when the patient voluntarily attempts to swallow, he or she will trigger a reflex more rapidly". As well as the effect of taste on swallowing, Kaatzke-McDonald et al. (1996) also studied the effect of cold (cold vs tepid) and touch (three strokes to the anterior faucial pillars vs feigned stimulation) stimulation of the anterior faucial pillar on human healthy swallowing. They found that cold touch simulation evoked a significant increase in swallowing latency and repetitive frequency of swallowing. The results suggest that there are thermo-sensitive receptors in the faucial pillars that evoke swallowing when simulated by cold touch. However, at the same time, Ali et al. (1996) reported that normal pharyngeal swallow response is neither facilitated nor inhibited by prior cold tactile stimulation or topical anesthesia of the tonsillar pillars. In 2003, Sciortino et al. reported results in accordance with Kaatzke-McDonald et al. (1996). Using surface electromyography (EMG), they showed that latency to swallow specific activity was significantly shorter following mechanical+cold+gustatory condition compared to no stimulation in a healthy population. This quicker swallow specific activity occurred only on the first swallow following stimulation. Only the treatment condition that employed all three types of stimuli together resulted in a significantly quicker average initiation of swallow activity when compared to the no stimulation condition. The reason why only the conjugated stimulus has an effect is not clear for the authors. The three hypotheses proposed credit the oropharyngeal sensory receptors in influencing swallow events and therefore individual stimulus should have an effect of the swallowing function. The three hypotheses proposed are the following: 1) thermal and tactile stimulation of the anterior faucial pillars may upregulate the mucosal receptors, thus lowering the threshold to evoke the subsequent pharyngeal swallow; 2) stimulation to the anterior faucial pillars increases "oral awareness" thus serving as a higher level alerting mechanism that facilitates the swallow response; 3) the swallow response threshold remain unchanged, however the summation of receptor activity in response to the greater sensory input leads to the quicker swallow response.

We can as well wonder if the effect of the viscosity of food on improving swallowing in dysphagia patients is only due to the physical properties of food (better cohesiveness/elasticity reduces the aspiration) and/or the perception of the food viscosity plays also a role. Smith et al. (1997 & 2006) argued that "altering the consistency of fluids is a common compensatory technique used in dysphagia management to facilitate change. However, it is not known what variations in viscosity can be perceived in the oral cavity or oropharynx. Knowing something of the perception of viscosity orally may assist with determining the precision required in prescribing alterations in viscosity for dysphagia individuals." Smith et al. evaluated the physical and perceived viscosity of samples in different proportions of water and corn syrup. The relation between physical viscosity and orally perceived viscosity could be stated as a power law: s=k where s is the psychological magnitude, is the intensity of the physical stimulus, k is a constant determined by the choice of unit selected for measurements and the exponent. Smith et al. (2006) found an exponent for oral perception of fluid viscosity of 0.3298, i.e. the oral sensation of viscosity grows at approximately a third of the rate of the actual viscosity. They suggested that as viscosity is concerned, well controlled viscosity property may not be necessary due to the low viscosity sensitivity. However, studies were conducted on Newtonian fluids (water and corn syrup mixed in different proportion) which is not the viscosity behaviour property of thickening agents. Most of them are shear thinning fluids. It would be interesting to investigate if viscosity perception helps in triggering swallowing. In the NDD guidelines, a range of viscosity is given for the three different consistencies (nectar, honey, pudding).

Therefore, the following specialized dysphagia treatment products can be provided to the patient based on the screening and diagnosis results:
a. Pre-made nutritional formulations already having beneficial dysphagia ingredients added
b. Modules (beneficial dysphagia ingredients added as prescribed/needed)
  i. Added to a standard base
  ii. Added to a liquid
    1. Water, juice, coffee, tea, ONS
  iii. Added to other food product
    1. Adding probiotics to a pureed food, gravy, jello, pudding
c. Elastic/viscous nutritional products
  i. Thickeners
    1. Those that maintain elasticity and viscosity after exposure to pressure of tongue on soft and/or hard palate
      a. Xanthan—Appropriate for use in persons with upper dysphagia.
    2. Those that lose elasticity and viscosity after exposure to pressure of tongue on soft and/or hard palate
      a. Starch—Appropriate for use in persons with upper and lower dysphagia
    3. Specific blends of thickeners that maintain a minimum level of elasticity and viscosity after exposure to pressure of tongue on soft and/or hard palate
      a. e.g. xanthan and starch—Appropriate for use in persons with upper dysphagia
    4. Amount of thickening
      a. Effective levels (nectar, honey, pudding, etc., viscosity measures)
  ii. Compositions that reduce pathogenic bacteria that are swallowed (improve oral health)—reduce aspiration pneumonia 1. Probiotics
   a. Probiotic strains indigenous to humans such as the *streptococcus Salivarius* K12 or *lactobacillus reuteri* will be used.
   b. *Streptococcus salivarius* K12, which produces produce salivaricin A and B, in testing has been shown to be effective against *Streptocous pyogenes, Micrococcus luteus, Streptococcus anginosis, Eubacterium saburreum, Micromonas micros, Moraxella, Prevotella intermedia,* and *Porphyomonas gingivalis,*
   c. *Lactobacillus reuteri* ATCC55730, which produces reuterin, in testing has been shown to be effective against: *Streptococcus mutans*, EHEC *Escherichia coli*, ETEC *Escherichia coli*, *Salmonella enterica, Shigella sonnei, Vibrio cholerae.* Additionally, *Lactobacillus reuteri* ATCC55730 has a commensal effect on *L. casei* ATCC 334, *L. johnsonii* ATCC33200, *L. acidophilus* ATCC 4356, *L. gasseri* ATCC 33323, *Clostridium difficile, Eubacterium eligens, Bifidobacterium longum* var infantis, *Eubacterium biforme, Bifidobacterium longum, Bifidobacterium catenulatum, Bacteroides vulgatus,* and *Bacteroides thetaiotaomicron.*
   d. *Lactobacillus johnsonii* La1, which produces H2O2, in testing has been shown to be effective against: *Escherichia coli* (ETEC, EPEC), *Salmonella typhimurium, Yersinia pseudotuberculosis, Helocobacter pylori,* Toxin A from *Clostridium difficile, Shigella flexneri, Klebsiella pneumoniae, Pseudomonas aeruginosa, Enterobacter cloacae, Staphylococcus aureus,* and *Listeria monocytogenes.*
   e. *Lactobacillus plantarum* 299v has been shown to help prevent colonisation of pathogens, and aids in preventing ventilation associated pneumoniae (VAP). Testing has shown that LP299v is effective against: *Streptococcus mutans, Streptococcus sobrinus,* and *Escherichia coli.*
   f. *Lactobacillus rhamnosus* GG has also been shown to help prevent colonisation of pathogens, and aids in preventing ventilation associated pneumoniae (VAP). Testing has shown that *Lactobacillus rhamnosus* GG is effective against *Streptococcus mutans, Streptococcus sobrinus,* and *Escherichia coli.*
   g. *Streptococcus thermophilus* NCC 1561, in testing has been shown to be effective against *Actinomyces viscosus,* and *Strepotcoccus sobrinus.*
   h. *Lactococcus lactis* NCC2211 (Pelargon strain), in testing has been shown to be effective against *Actinomyces viscosus* and *Strepotcoccus sobrinus.*

Examples of Non-Replicating Micro-organisms include
   i. Lacteol which acts by a mechanism of inhibition of adhesion of pathogens (adheres to Caco 2 and HT29-MRX cells) and has been shown in testing to prevent adhering of *Lysteria monocytogenes,* ETEC *Escherichia coli,* EPEC *Escherichia coli, Yersinia pseudotuberculosis,* and *Salmonella typhimurium.* Additionally, Lacteol has been shown to have antimicrobial activity against: *Staphylococcus aureus, Listeria monocytogenes, Bacillus cereus, Salmonella typhimurium, Shigella flexneri, Escherichia coli, Klebsiella pneumoniae, Pseudomonas aeruginosa,* and *Enterobacter* spp.

Other Ingredients with desired properties in accordance with the present invention include:
   j. CGMP which has been shown in testing to prevent binding of pathogens and is known to be effective against *Streptococcus mutans* and *Streptococcus sobrinus.*
2. Can be added to liquids, semisolids and solids iii. Compositions that trigger/enhance swallow reflex, including combinations of those listed below, for example: Sucrose+vanilla, Citric acid+lemon, Menthol+cooling agent, and Citric acid+Menthol+cooling agent.
   1. basic tastants
      a.—Sucrose
      b.—Artificial sweeteners
      c.—Citric acid
      d.—Salt
      e.—Caffeine
      f.—sucrose/citric acid
      g.—salt/citric acid
   2. trigeminal stimulants
      a. Vanilloid receptor 1 ("VR-1") agonists
         i. Capsaicin, capsinoids, capsiate, dihydrocapsaicin, dihydrocapsiate, nordihydrocapsaicin, nordihydrocapsiate, homocapsaicin, homodihydrocapsaicin, vanillylamide of n-nonanoic acid ("VNA"), anandamide, resiniferatoxin, and olvanil
            1. Non-pungent varieties—As used herein, the terms "non-pungent" refer to vanilloid receptor agonists that elicit minimal, or no, sharp or biting sensations or sensations of heat. Capsiate has been extracted from a non-pungent cultivar of red pepper, CH-19 sweet, and shown to be a capsaicin analogue called capsinoid that has an ester bond instead of the amide bond between the vanillyl moiety and fatty acid chain.
      b. Cooling agent
      c. Cold temperature of the food or drink
   3. Aromas
      a. Lemon
      b. Vanilla
      c. Menthol
   4. Salivating agents
   5. Aerated compositions (i.e. carbonation)
   6. Angiotensin-conversation enzyme ("ACE") inhibitor
      i. Dietary source (e.g., bioactive peptides)
      ii. synthetic source (as found in prescription drugs)

The dysphagia treatment products can be prepared as follows:
   a. At-home delivery of standardized nutritional products for dysphagia management (e.g., ready-to-drink thickened beverages, pureed foods & mixes)
   b. Tools for ensuring that manually-prepared products are in accordance with standardized product specifications (e.g. line spread test calibrated to appropriate liquid consistencies; kit of funnels of various sizes; specially-calibrated hand held viscometer device; recipes and/or cookbook [electronic or print material]; online instructions/training programs for caregivers [e.g., formal and informal]).

Innovative Thickening Agent

An innovative thickening agent that enables the dysphagic patient or caregiver to achieve the minimum swallow-safe bolus viscosity with ease. This would help to provide peace of mind to caregivers concerned about providing what is medically appropriate/in line with best practice guidelines. It would make it more convenient for patients/caregivers to do what is guideline-recommended as medically appropriate. Additionally, it helps to alleviate the stress of adapting to lifestyle changes required following dysphagia diagnosis. This innovative thickening agent will increase compliance with the prescribed treatment (the recommended swallow-safe bolus viscosity), and aid in avoiding the common clinical complications in dysphagia patients and their associated costs and burdens, both physical and economic on the healthcare system. This new thickening agent will help to optimize clinical and economic outcomes and improve the quality of dysphagia patient care.

Diet modification is currently the mainstay of therapy for oro-pharyngeal dysphagic patient to reduce complications, including the risk of aspiration pneumonia. The strongest evidence-based recommendation that can be made is to modify the bolus viscosity. Clinical practice guidelines support the routine implementation of this intervention for persons with dysphagia. Standardized terminology and definitions of fluid viscosity modification for dysphagia patients have been established. In particular, the National Dysphagia Diet, developed by a multi-disciplinary taskforce in the US in 2002, is accepted as the standard for dietary treatment of dysphagia. Two tenets of the National Dysphagia Diet included recommending labeling (thin, nectar-like, honey-like, and spoon-thick) and viscosity ranges for each category of thickened liquids.

With the average commercial thickening agent, the preparation of liquids thickened to the guideline-recommended fluid viscosity is left to subjective judgement. The manufacturers suggest dosage ranges for each liquid to be thickened for individuals with dysphagia. The provision of different dosage ranges for each liquid permits wide variation in the amount of thickening agent used, and can result in a liquid that is inadequately thickened and thus is at greater risk of aspiration. In addition, preparation of appropriately thickened liquids becomes more of a chore as subjective judgement of consistency (stirring, oral manipulation, etc.) is not a valid method for determining that a liquid has been thickened to the intended bolus viscosity. Objective measurements (i.e., with use of a viscometer) promotes consistent preparation of liquids thickened to the appropriate bolus viscosities with typical commercial thickening agents. However, viscometers are rather expensive and are usually only available in laboratory settings. Furthermore, it would be labor-intensive to check the viscosity of each liquid (that is likely to vary in composition and temperature) prior to serving it to an individual with dysphagia. In principal, increasing the viscosity of fluids using commercial thickening agents decreases the rate of flow, allowing patients more time to initiate airway protection and prevent or decrease aspiration while swallowing. Thus, serving a liquid that is outside the recommended fluid viscosity range can be dangerous to dysphagia patients, increasing the risk of complications, including aspiration and aspiration pneumonia.

Currently, many commercial thickening agents have complex mixing instructions, depending on the liquid or liquid-temperature intended to thicken. The potential for error in preparing thickened liquids increases with average commercial thickening agents. Based on the performance features of this innovative thickening agent, ThickenUp Clear enhances swallowing safety among individuals with dysphagia.

With ThickenUp Clear, the minimum guideline-recommended bolus viscosity is achieved by using a single dosage amount for the various liquids and liquid-temperatures studied.

Resource ThickenUp Clear achieves the bolus viscosity recommended by guidelines with the use of:
- 1.2 g/100 ml of liquid to achieve nectar-like thickened liquids
- 3.6 g/100 ml of liquid to achieve honey-like thickened liquids, at minimum
- 8.4 g/100 ml of liquid to achieve pudding-like thickened liquids The ability to achieve the minimum bolus viscosity is consistent for:
- A range of liquids
- A range of liquid-temperatures The appropriate dosage amount can be easily achieved with a uniform scoop or sachet/stickpak. Patients can continue to use the same purchased product even if the prescribed intervention changes (e.g., from honey to nectar). For example, for an eight ounce serving:
- Use one scoop/stickpak of ThickenUp Clear to achieve nectar-like thickened liquids.
- Use three scoops/stickpaks of ThickenUp Clear to achieve honey-like thickened liquids.
- Use seven scoops/stickpaks of ThickenUp Clear to achieve pudding-like thickened liquids.

Unlike other commercial thickening agents, the minimum bolus viscosity can be achieved by using a single dosage amount for a range of liquids and liquid-temperatures, making it easier for the patient or caregiver to prepare appropriately thickened liquids.

In an embodiment, the method is performed using a computer process. For example, one or more of the screening, diagnosing, categorizing, choosing and giving steps can be utilized as part of an algorithm implemented in a computer program. The computer program can be run by the HCP or the patient themselves. Any specified dysphagia treatment products can be provided to the patient after the proper treatment has been chose.

In an alternative embodiment, the present disclosure provides a method for providing treatment for a patient having dysphagia at a care center. The method comprises screening the patient for dysphagia symptoms, diagnosing and categorizing the dysphagia if the patient exceeds a threshold of dysphagia symptoms, and providing the patient products and services to facilitate rehabilitation of the patient at the care center. Accordingly, the care center can provide comprehensive resources, facilities and dysphagia treatment products to treat patients having or at risk of having dysphagia.

In yet another embodiment, the present disclosure provides a method for generating revenue by treating a patient having dysphagia at a care center. The method comprises screening the patient for dysphagia symptoms, diagnosing and categorizing the dysphagia if the patient exceeds a threshold of dysphagia symptoms, providing the patient at least one product or service to facilitate rehabilitation of the patient at the care center, and charging the patient a fee depending on the product or the service. In alternative embodiments, the patient can be charged a fee at one or more of the other steps of the treatment process or as part of a comprehensive treatment plan.

In still another embodiment, the present disclosure provides a kit for providing treatment for a patient having dysphagia. The kit comprises: (i) a screening tool that screens the patient for dysphagia, (ii) a diagnostic test that categorizes the dysphagia if the patient exceeds a threshold of dysphagia symptoms, (iii) a suggested course of dysphagia treatment based the patient's dysphagia, and (iv) instructions for implementing the dysphagia treatment. The kit can contain a comprehensive set of screening and diagnostic tools and dysphagia treatment products/instructions for dysphagia treatment physical therapies to treat patients having or at risk of having dysphagia. The kit can be sold at a general store, hospital or a dysphagia care center.

In another embodiment, the present disclosure provides a method of reducing healthcare costs associate with dysphagia. By evaluating and identifying swallowing impairments in an early phase (e.g., by widespread implementation of standardized, evidence-based methods of dysphagia screening and management), appropriate early management of swallowing impairments and be enabled and implemented. This can reduce morbidity and mortality, reduce fear and pain, and improve quality of life.

The economic benefits of the methods in alternative embodiments include avoiding the treatment costs of the clinical complications of dysphagia (e.g. pneumonia, recurrent pneumonia, dehydration, and malnutrition and related complications). These costs may be associated with:

- Hospitalizations, re-hospitalizations, transitional care (e.g., subacute care), and physicians office visits/follow-up care.
- Specialized care (emergency room visits, artificial ventilation, treatment for dehydration[IV fluids], antibiotic use & related complications [nosocomial infection with 'superbugs' such as MRSA and *c.difficile*], costs & extended stays associated with opportunistic infections [e.g. UTIs] during periods of systemic inflammation [as the body is only able to launch an insufficient immune response that fails to protect the host from microbial challenge], pulmonary rehabilitation post-ventilation.
- Chronic conditions and/or exacerbated conditions (e.g., diseases associated with chronic inflammation such as cardiovascular disease, diabetes, metabolic syndrome, cachexia).
- Poor health outcomes that arise following an acute insult such as pneumonia or acute stroke (e.g., downward spiral in health among elderly; malnutrition and its consequences [e.g., pressure ulcers, infection, slowed recovery, greater healthcare utilization]; more-severe dysphagia; loss of functionality, autonomy, and mobility; increased caregiver burden, frailty; dementia; falls and related injuries [e.g., fractures].)

The benefits derived from better treatment include improving an individual's ability and efficiency to swallow improves the individual's safety through reduced risk of pulmonary aspiration. An efficient swallow may permit greater independence from feeding assistance and/or reduced length of time spent in feeding-assistance during meal consumption and improved quality of life. Efficient swallow also reduces the viscosity of liquids required for safety (e.g., pudding, honey and nectar thickness products) and may also limit the use of texture-modified foods. All of these previously described factors are aimed at improving an individual's quality of life.

Additional health and economic benefits involve avoiding the pain, distress, and costs associated with the consequences of malnutrition (infection, pressure ulcers, increased severity of dysphagia, cachexia, and loss of autonomy increasing caregiver burden) and dehydration (death, falls secondary to electrolyte imbalance, etc.) and the loss of pleasure, psycho-social aspects of eating, and overall quality of life. Additionally, health and economic benefits are appreciated by avoiding the cost of clinical complications (e.g., recurrent pneumonia due to unrecognized underlying swallowing impairment) and medical errors (falls, infections, and pressure ulcers as a consequence of malnutrition/dehydration secondary to swallowing impairment); avoid fines, lawsuits, and settlement fees that result when patient care documentation reflects that care was not provided in accordance with established standards of care (e.g., dietary modification provided in line with the national standards, prompt nutrition and hydration screening for persons with swallowing impairment, assessment by and advice from a qualified professional in dysphagia management to assist in developing strategies to maintain oral intake, etc., swallowing rehabilitation interventions that include dietary modification, postural positioning, compensatory swallowing strategies, thermal stimulation, and oral motor exercises; and the provision of a range of modified texture foods and fluids as recommended by speech language pathologists ["SLPs"] for their patients).

Considering current care practices, a large discrepancy exists in the management of dysphagia. A standardized approach to dysphagia patient care that incorporated evidence-based methods in accordance with embodiments of the present disclosure can improve the lives of a large and growing number of persons with swallowing impairments. Specific interventions (e.g. to promote oral health, help restore normal swallow, or reinforce a swallow-safe bolus) can enable persons to eat orally (vs. being tube fed and/or requiring PEG placement) and experience the psycho-social aspects of food associated with general well being while guarding against the clinical complications that arise from lack of diagnosis and appropriate early management of dysphagia.

EXAMPLES

By way of example and not limitation, the following examples are illustrative of various embodiments of the present disclosure.

The Cereal Test—In order to diagnose a good swallowing, a standardized weight of commercial wheat flake cereals can be given to subjects (e.g. 3 gram amount). Different types of cereal flakes can be used. The mastication behavior can be observed based on two parameters: (i) mastication time, and (ii) number of cycles. For healthy subjects, on average, wheat flake cereals are eaten in 26+/−2 s and 38+/−2 cycles. A food bolus just before swallowing needs to be collected and characterized physically.

In order to collect the food bolus just before swallowing, the subject is asked to expectorate the sample when he feels ready to swallow. He makes a hand sign to the experimenter, and expectorates the main part of the bolus formed in a receptacle retrieved by the experimenter. He does not rinse his mouth and does not collect the few particles dispersed in mouth. The addition of water and the collection of all particles dispersed in mouth could change the structure of the potential swallowable bolus.

Water contents of cereal and cereal boli need to be measured to determine the salivation and food water intake capacities. All the samples are dried at 130° C. for 120 minutes in an oven. For the cereal boli, samples are immediately weighted after expectoration to avoid weight loss due to water evaporation. After drying, samples are cooled down one hour in a dessicator, with a controlled temperature (around 25° C.) and humidity (35%), in order to stabilize the weight before weighting. The water content of cereal and cereal bolus is determined by the difference between the weight of cereal/cereal bolus before drying and the one after drying. Furthermore, the water intake of cereals during mastication is determined by the difference between initial water content of cereals and water content of cereal bolus at the end of mastication. It was found that for healthy people, water content of cereal food bolus should be around 50%.

The stimulated saliva flow of a subject can also be measured by asking him to drink two sips of water and then putting a Parafilm M® square (Pechiney Plastic Packaging, Chicago) folded in 4 in his mouth. The subject masticates this Parafilm square during one minute while swallowing his saliva. This first step helps in stabilizing the saliva flow. After one minute, the subject masticates one more minute but this time spits saliva in a small previously weighed receptacle. The receptacle of saliva is weighed to determine the stimulated salivary flow. For healthy people, saliva flow can vary from 0.6 to 3.9 ml/min with an average of 1.9 ml/min In order to determine the rheological properties of the cereal food bolus, small oscillation measurements (e.g. using a rheometer with cup/vane geometry) or texture profile analysis (e.g. using an instron instrument) could be carried out to determine the visco-elasticity properties and particle size distribution of material and therefore to check the good cohesiveness/stickiness of the food bolus before swallowing. For healthy people, it was found that a swallowable food bolus has a storage modulus comprise between 14 and 22 KPa, and a yield stress property varying from 1.3 to 4.3 KPa. By using the previously discussed test methods, saliva amounts, enzyme breakdown, and mastication effectiveness can be examined as components of or exacerbating factors in dysphagia.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of treating patients having dysphagia, comprising:
   screening a patient for a dysphagia risk, the screening comprises scoring a questionnaire based on answers from the patient to the questionnaire, the scoring provides a cumulative point total, and the screening further comprises determining the dysphagia risk of the patient based on the cumulative point total from the questionnaire;
   choosing a proper dysphagia treatment product if the cumulative point total exceeds a threshold, and the dysphagia treatment product comprises a component selected from the group consisting of probiotics, vanilloid receptor 1 agonists, angiotensin-conversation enzyme inhibitors, basic tastants, trigeminal stimulants, aromas, salivating agents, thickener compositions, aerated compositions, and combinations thereof;
   giving the patient preparation instructions for the dysphagia treatment product; and
   wherein the scoring of the questionnaire and the determination of the dysphagia risk are performed using an algorithm implemented by a computer.

2. The method of claim 1, wherein the questionnaire includes past information relating to dysphagia variables identified by caretaker review, observed variables and self-reported variables.

3. The method of claim 1, wherein the choosing the proper dysphagia treatment product is based on categorizing the patient based on the cumulative point total from the questionnaire and at least one step selected from the group consisting of:
   measuring a force exerted by a tongue of the patient on a soft and/or hard palate;
   determining if the airway and the epiglottis of the patient is closing completely;
   determining if the airway and the epiglottis timing of the patient is correct;
   performing a corn flake test on the patient;
   monitoring a tracheal pH of the patient for 24 hours;
   performing an ultrasound on the patient to detect abnormal oropharyngeal motor function;
   utilizing a deploy preparation tool; and
   performing an oral health assessment on the patient.

4. The method of claim 1, wherein the dysphagia treatment product comprises a probiotic selected from the group consisting of *Streptococcus salivarius* K12, *Lactobacillus reuteri* ATCC55730, *Lactobacillus johnsonii* La1, *Lactobacillus plantarum* 299v, *Lactobacillus rhamnosus* GG, *Streptococcus thermophilus* NCC 1561, *Lactobacillus lactis* NCC2211, Lacteol, and combinations thereof.

5. The method of claim 1, wherein the choosing step is performed by the algorithm.

6. The method of claim 1, wherein the proper dysphagia treatment product is chosen from a plurality of dysphagia treatment product that each have a different characteristic relative to each other.

7. The method of claim 1, wherein the patient preparation instructions include following dietary modifications in accordance with dysphagia treatment specifications.

8. A kit for use in a method comprising screening a patient for a dysphagia risk and choosing a proper dysphagia treatment product based on the screening, the kit comprising:
   a screening tool that screens the patient for the dysphagia risk, the screening tool comprising a questionnaire and further comprising a screening score system that determines the dysphagia risk of the patient based on a cumulative point total from answers to the questionnaire;
   a diagnostic test that categorizes the dysphagia based on the cumulative point total from the questionnaire;
   a suggested course of dysphagia treatment based the patient's dysphagia;
   instructions for implementing the dysphagia treatment; and
   a dysphagia treatment product comprising a component selected from the group consisting of probiotics, vanilloid receptor 1 agonists, angiotensin-conversation enzyme inhibitors, basic tastants, trigeminal stimulants, aromas, salivating agents, thickener compositions, aerated compositions, and combinations thereof.

9. The kit of claim 8, wherein the dysphagia treatment is a physical therapy regime of the patient based the patient's dysphagia.

10. The kit of claim 9, wherein the physical therapy regime comprises at least one therapy selected from the group consisting of:
    performing specific postural positioning during and after eating; and
    performing rehabilitative exercises.

11. The kit of claim 9, wherein the physical therapy regime is paired with an anabolic nutritional regime.

12. A method of treating patients for dysphagia, the method comprising using an algorithm implemented in a computer program to:
    screen a patient for a dysphagia risk by scoring a questionnaire based on answers from the patient to the questionnaire, the scoring providing a cumulative point total, and determining the dysphagia risk of the patient based on the cumulative point total from the questionnaire;

choose a proper dysphagia treatment product if the dysphagia risk exceeds a threshold, the dysphagia treatment product comprising a component selected from the group consisting of probiotics, vanilloid receptor 1 agonists, angiotensin-conversation enzyme inhibitors, basic tastants, trigeminal stimulants, aromas, salivating agents, thickener compositions, aerated compositions, and combinations thereof; and provide the patient preparation instructions for the dysphagia treatment product.

* * * * *